(12) United States Patent
Zaneveld et al.

(10) Patent No.: US 6,537,538 B2
(45) Date of Patent: Mar. 25, 2003

(54) METHOD FOR THE PREVENTION, INHIBITION, OR TREATMENT OF VAGINITIS AND/OR BACTERIAL VAGINOSIS USING POLYSTYRENE SULFONATE

(75) Inventors: Lourens Jan Dirk Zaneveld, Chicago, IL (US); Robert Anthony Anderson, Jr., Chicago, IL (US)

(73) Assignee: Rush-Presbyterian-St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/739,945

(22) Filed: Dec. 18, 2000

(65) Prior Publication Data

US 2002/0114776 A1 Aug. 22, 2002

(51) Int. Cl.$^7$ .............................................. A61K 31/74
(52) U.S. Cl. .................... 424/78.07; 424/430; 424/422; 424/78.08; 424/78.02; 424/78.05
(58) Field of Search .......................... 514/967; 424/430, 424/422, 78.08, 78.02, 78.05, 78.07

(56) References Cited

U.S. PATENT DOCUMENTS

| | | | |
|---|---|---|---|
| 5,308,612 A | 5/1994 | Lee | 424/78.35 |
| 5,314,904 A | 5/1994 | Egidio et al. | 514/394 |
| 5,536,743 A | 7/1996 | Borgman | 514/39.8 |
| 5,804,179 A | * 9/1998 | Bruce et al. | 424/93.45 |
| 5,814,329 A | * 9/1998 | Shah | 514/967 |
| 5,840,744 A | 11/1998 | Borgman | 514/398 |
| 6,017,521 A | 1/2000 | Robinson et al. | 424/78.02 |
| 6,125,850 A | 10/2000 | Sokal et al. | 128/830 |

FOREIGN PATENT DOCUMENTS

WO WO 00 69428 * 11/2000

OTHER PUBLICATIONS

Chem. Ab. 134:95617 R. Anderson et al 2000.*
Chem. Ag. 128:162578 L. Zeitlin et al 1997.*
Mandell, G. L., et al., *Principles and Practice of Infectious Diseases,* vol. 1, Ch. 95, pp. 1218–1235 (5$^{th}$ Edition, 2000).
Breen, J., *The Gynecologist and the Older Patient,* (ed.) p. 304–305 (1988).
Berkow, R. (Editor–in–Chief), *The Merck Manual of Medical Information: Home Edition,* (1997), pp. 1081–1083.

* cited by examiner

Primary Examiner—Thurman K. Page
Assistant Examiner—Liliana Di Nola-Baron
(74) Attorney, Agent, or Firm—Fitch, Even, Tabin, & Flannery

(57) ABSTRACT

A method for preventing, inhibiting, or treating vaginitis or bacterial vaginosis using polystyrene sulfonate is provided. The polystyrene sulfonate used in the present invention inhibits Trichomonas (a flagellate protozoon), Gardnerella, and other vaginitis/vaginosis-causing bacteria. The method of this invention generally comprises the application of an effective amount of an inhibitory agent into the vagina of a female in need of prevention, inhibition, and/or treatment of vaginitis and/or bacterial vaginosis. Preferably the polystyrene sulfonate in contained in an aqueous based composition, more preferably in an aqueous based composition buffered to a pH of about 3.5 to about 7.5, and even more preferably in an aqueous based composition buffered to a pH of about 3.5 to about 5.

24 Claims, No Drawings

METHOD FOR THE PREVENTION, INHIBITION, OR TREATMENT OF VAGINITIS AND/OR BACTERIAL VAGINOSIS USING POLYSTYRENE SULFONATE

FIELD OF THE INVENTION

This invention generally provides a method for preventing, inhibiting, or treating vaginitis or bacterial vaginosis. More specifically, the present invention provides a method for preventing, inhibiting, or treating vaginitis and/or bacterial vaginosis using polystyrene sulfonate. The polystyrene sulfonate used in the present invention inhibits Trichomonas (a flagellate protozoon), Gardnerella, and other vaginitis/vaginosis-causing bacteria.

BACKGROUND OF THE INVENTION

The female vagina is colonized by a variety of bacteria. Under normal conditions, the vagina flora provides a protective mechanism, including the maintenance of a low pH, to guard against the invasion of pathogenic microbes. A normal vagina generally contains more than about $10^4$ lactobacilli per milliliter of vaginal material.

Infectious vaginitis is a common clinical syndrome and is diagnosed in more that 25 percent of women visiting sexually transmitted disease clinics. Common symptoms of infectious vaginitis include, for example, disruption of the normal vagina flora, irritation, odor, and/or vaginal discharge. Infectious vaginitis or vulvovaginities includes Candidiasis, trichomoniasis, bacterial vaginosis, and other vaginal infections. Bacterial vaginosis is the most common form of infectious vaginitis, accounting for 45 percent of symptomatic cases and estimated to be present in 15 percent of asymptomatic sexually active women. See, e.g., *The Gynecologist and the Older Patient*, Breen, J. (ed.), pp. 304–305 (1988); *Principles and Practice of Infectious Diseases*, Mandell, G. L., J. E, Bennett, & R. Dolin (eds.), vol. 1, ch. 95, pp. 1218–1235 (5th Edition, 2000); *The Merck Manual of Medical Information: Home Edition*, Berkow, R. (Editor-in-Chief, 1081–1083 (1997). Bacterial vaginosis is a polymicrobial vaginal infection believed to be caused by an increase in the number of anaerobic organisms with a concomitant decrease in lactobacilli in the vagina. The decrease in the number of lactobacilli in the vagina has a dual effect, i.e., (1) a decreased competition for nutrients and (2) a decrease in the amount of lactic acid present (i.e., increasing the pH), thus allowing for the multiplication of opportunistic pathogens in the vagina, whose growth is normally suppressed by the lactobacilli and the acidic pH of the vagina. The principal pathogens associated with bacterial vaginosis are believed to be *Gardnerella vaginitis* and other pathogenic anaerobes. Thus, bacterial vaginosis is considered a broad spectrum infection requiring a broad spectrum treatment.

Clinically, bacterial vaginosis presents itself as a superficial vaginal infection with no inflammatory response. Generally symptoms include an unpleasant smell, an elevated vaginal pH greater than about 5.0, a thin homogeneous discharge, and the presence of Gardnerella clue cells (i.e., vaginal epithelial cells coated with small Gram-variable rods). Generally, lowering the vaginal pH is an effective measure against the infection.

Generally, current treatment regimens for bacterial infection of the vagina, including vaginosis, involve the use of various broad spectrum antibiotics administered either topically or orally. The following table illustrates some of the current treatments for common vaginal/vulvar infections:

| Infection Type | Common Treatment |
| --- | --- |
| Candidal (yeast) | miconazole, clotrimazole, butoconazole, or terconazole (cream, vaginal tablets, vaginal suppositories); fluconzole or ketoconazole (oral) |
| Bacterial | metronidazole (vaginal cream or oral), clindamycin (vaginal cream), or rifaximin (vaginal foam or cream) |
| Trichomonal | metronidazole (oral) |

Antibiotics are generally undesirable, however, because they may kill a broad range of the normal bacterial flora in the vagina, including the beneficial lactobacilli. This may cause secondary complications, since the lactobacilli keep various opportunistic pathogens in the vagina in check. The treatment might then necessitate a further treatment regimen, such as the ingestion of cultured dairy products to replace the lactobacilli in the body, as well as treatment by antifungal agents. Moreover, a rise in the level of anaerobes due to a lack of lactobacilli could further complicate the infection. Additionally, antibiotics, when used frequently within the vagina, can cause systemic toxicity through absorption from the vagina.

More recently developed treatment regimes include those provided in U.S. Pat. No. 5,536,743 (Jul. 16, 1996) and U.S. Pat. No. 5,840,744 (Nov. 24, 1998) which used metronidazole in a buffered composition (pH maintained at about 3.75 to about 4.25) for intravaginal treatment of bacterial vaginosis. U.S. Pat. No. 6,017,521 (Jan. 25, 2000) provided a bioadhesive aqueous composition to control vaginal pH and, therefore, alleviate microorganism growth and odor such as presented by bacterial vaginosis.

U.S. Pat. No. 5,308,612 (May 3, 1994) provides a method using polystyrene sulfonate to inhibit or antagonize the transactivating transcription factor (Tat) of HIV/AIDS; the polystyrene sulfonate was reported to bock HIV replication as well as HIV viral adhesion and infection. U.S. patent application Ser. No. 09/252,417, filed Feb. 18, 1999, provides a method using polystyrene sulfonate for preventing sexually transmitted diseases (STDs) and/or reducing the rate of transmission of such sexually transmitted diseases; this method is especially adapted for use by sexually active individuals not at risk for pregnancy. U.S. patent application Ser. No. 09/252,417 is hereby incorporated by reference.

It would still be desirable, however, to provide improved methods for preventing, inhibiting, or treating vaginitis or bacterial vaginosis. It also would be desirable if such improved methods for preventing, inhibiting, or treating vaginitis or bacterial vaginosis did not involve the use of antibiotics. It would also be desirable if such methods would assist in obtaining or maintaining the natural and protective vaginal mechanisms. It would also be desirable if such methods would be relatively easy to use and have relatively few side effects. It would also be desirable if such methods utilize an active ingredient that is not absorbed, or only minimally absorbed, through the vagina lining, thereby greatly decreasing or eliminating the chance for systemic toxicity. The present invention, as detailed in the present specification, provides such methods.

SUMMARY OF THE INVENTION

This invention generally provides a method for preventing, inhibiting, or treating vaginitis or bacterial vaginosis. More specifically, the present invention provides a method for preventing, inhibiting, or treating vaginitis and/or bacterial vaginosis using polystyrene sulfonate. The polystyrene sulfonate used in the present invention inhibits Trichomonas (a flagellate protozoon), Gardnerella, and other vaginitis/vaginosis-causing bacteria.

The method of this invention generally comprises the application of an effective amount of an inhibitory agent into the vagina of a female in need of inhibition and/or treatment of vaginitis and/or bacterial vaginosis. Preferably the polystyrene sulfonate is contained in an aqueous based composition, and more preferably in an aqueous based composition buffered to a pH of about 3.5 to about 7.5, and even more preferably buffered at a pH of about 3.5 to 5.

The polystyrene sulfonate compositions of this invention can be used for treatment of active cases of vaginitis and/or bacterial vaginosis. Since the compositions of the present invention cause few, if any side effects, the polystyrene sulfonate compositions of this invention can also be used for prophylactic purposes. The polystyrene sulfonate used in the present invention is generally not toxic (or only minimally toxic) to natural and beneficial vaginal flora and, thus, does not significantly upset the local microbiological balance or significantly disrupt the protective glycoprotein vaginal coating. Disruption of the natural vaginal flora and/or removal or disruption of the protective glycoprotein vaginal coating using conventional vaginal compositions (e.g., contraceptives and the like) can lead to further irritation of the vaginal wall and/or lesions on the vaginal wall. Moreover, the preferred polystyrene sulfonate used in the present invention generally has a sufficiently high molecular weight to make vaginal absorption highly unlikely, thereby minimizing concern for systemic toxicity.

The present invention provides a method for the prevention, inhibition, or treatment of vaginitis and/or bacterial vaginosis in a female, said method comprising administering an effective amount of a polystyrene sulfonate composition into the vagina of the female.

The present invention also provides a method for the control and inhibition of Trichomonas, Gardnerella, or other vaginitis/vaginosis-causing bacteria in the vagina of a female, said method comprising administering an effective amount of a polystyrene sulfonate composition into the vagina of the female, wherein the effective amount of polystyrene sulfonate is sufficient to control and inhibit Trichomonas, Gardnerella, or other vaginitis/vaginosis-causing bacteria.

The present invention also provides a prophylactic treatment method for reducing the risk of vaginitis and/or bacterial vaginosis in a female, said method comprising administering an effective amount of a polystyrene sulfonate composition into the vagina of the female who may be at risk of vaginitis and/or bacterial vaginosis but is not suffering from vaginitis and/or bacterial vaginosis, wherein the effective amount of polystyrene sulfonate is sufficient to reduce the risk of Trichomonas, Gardnerella, or other vaginitis/vaginosis-causing bacteria from becoming established within the vagina.

The present invention also provides a method for the selective prevention, inhibition, or treatment of vaginitis and/or bacterial vaginosis in a female without significantly disrupting normal vaginal flora, said method comprising administering an effective amount of a polystyrene sulfonate composition into the vagina of the female, wherein the effective amount of polystyrene sulfonate is sufficient to inhibit Trichomonas, Gardnerella, or other vaginitis/vaginosis-causing bacteria without significantly disrupting normal vaginal flora.

Preferably the polystyrene sulfonate compositions used in the present invention comprise polystyrene sulfonate in an aqueous base buffered at a pH of about 3.5 to about 7.5, and even more preferably buffered at a pH of about 3.5 to 5. Preferably the polystyrene sulfonate composition contains about 10 to about 250 mg/ml polystyrene sulfonate having a molecular weight greater than about 100,000 g/mole. Even more preferably the polystyrene sulfonate composition contains about 20 to about 100 mg/ml polystyrene sulfonate having a molecular weight greater than about 200,000 g/mole.

These and other advantages of the present invention will be apparent from a consideration of the present specification.

DETAILED DESCRIPTION OF THE INVENTION

This invention generally provides a method for preventing, inhibiting, or treating vaginitis or bacterial vaginosis. More specifically, the present invention provides a method for preventing, inhibiting, or treating vaginitis and/or bacterial vaginosis using polystyrene sulfonate. The polystyrene sulfonate used in the present invention inhibits Trichomonas (a flagellate protozoon), Gardnerella, and other vaginitis/vaginosis-causing bacteria.

The method of the present invention is carried out by applying an effective amount of polystyrene sulfonate into the vagina of a female needing, or desiring, such treatment. For purposes of this invention, an "effective amount" is an amount of polystyrene sulfonate sufficient to inactivate, but not necessarily kill, bacteria or other microorganisms responsible for vaginitis or bacterial vaginosis on contact. Such bacteria or other microorganisms include, for example, Trichomonas, Gardnerella, and other vaginitis/vaginosis-causing bacteria.

Generally, the polystyrene sulfonate is incorporated into conventional carriers, such as, for example, lotions, creams, jellies, liniments, ointments, salves, oils, foams, gels, tablets, films, washes, suppositories, slow-releasing polymers, coatings, devices, and the like so that they can be easily applied topically in the present methods. The carriers may also include other ingredients such as, for example, pH modifiers, stabilizers, buffers, surfactants, moisturizers, colorants, thickeners, flavorings, fragrances, perfumes, and the like. The polystyrene sulfonate compositions of the present invention may be used by both sexually inactive and sexually active females. The polystyrene sulfonate compositions of the present invention may also be used with conventional birth-control or safe-sex devices. For example, the polystyrene sulfonate compositions could be incorporated into or simply used in conjunction with condoms (i.e., via lubricants applied to the interior and/or exterior surfaces), diaphragms, cervix caps, or similar products. The polystyrene sulfonate compositions of the present invention could also, for example, be released into the vagina by hand, via gels or suppositories, or by using conventional tampon or syringe techniques. The method of administering or delivering the polystyrene sulfonate composition into the vagina is not critical so long as an effective amount of polystyrene sulfonate is delivered in a timely manner. Preferably the formulations and/or method of delivering polystyrene sulfonate allows the polystyrene sulfonate compositions to remain within the vagina for an expended period of time (i.e., preferably for more than about 2 hours after administration) even during or after sexual activity in order to maximize the effectiveness.

Generally, the polystyrene sulfonate is employed at a concentration of about 5 mg/ml or higher in a suitable formulation, preferably at a concentration of about 10 mg/ml to about 250 mg/ml, and more preferably at a concentration of about 20 mg/ml to about 100 mg/ml based on the total weight of inert and active ingredients. Although it is generally preferred that the polystyrene sulfonate is used at noncytotoxic levels in order to minimize potential side effects, it can also be used, if desired, at levels at which bacteria or other microorganisms responsible for vaginitis or bacterial vaginosis (or a significant portion thereof) are effectively killed rather than simply inactivated or inhibited.

In actual use, polystyrene sulfonate in a suitable carrier or vehicle is applied, preferably topically, into vagina using any suitable technique (e.g., by hand, via gel or suppositories, or by using conventional tampon or syringe techniques). Of course, it is preferred that treatment begin as quickly as possible after the appearance of symptoms relating to vaginitis or bacterial vaginosis. The compositions of this invention can be reapplied as needed. Generally the composition is reapplied every about 12 to about 24 hours until control is obtained. For prophylactic purposes, treatment about once a day is usually sufficient. Of course, the frequency of application for either treatment or prophylactic purposes can vary with a number of factors, including, for example, the individual female and/or the severity of the infection.

The polystyrene sulfonate active ingredient used in this invention does not significantly affect or inhibit the growth characteristics of the normal vaginal flora or otherwise significantly irritate the vaginal tissue when used at inhibitory, noncytotoxic, or clinical concentrations. No toxicity was observed towards the host cells at the concentration ranges of polystyrene sulfonate used. Tests confirm there is essentially no effect on lactobacillus growth in the presence polystyrene sulfonate even at concentrations of up to about 5000 $\mu$g/ml. Thus, the beneficial components of normal vaginal flora are not disrupted by the use of the present invention. Significant inhibition or modifications of the vaginal flora or other irritations (such as when nonoxynol-9 is used) can lead to increased risks of infections, unusual discharges, general discomforts, and the like, which, in turn, can lead to a reluctance to use or fully take advantage of the treatment method. Such inhibition or modifications of the vaginal flora can also lead to irritation of vaginal tissue and/or lesions which can actually increase the risk of infection by other undesirable organisms. Moreover, because the polystyrene sulfonate compositions of the present invention do not significantly disrupt normal vaginal flora, these compositions are ideally suited for use in prophylactic treatment regimes. Thus, a woman, based on her personal history, may wish to use these compositions in a prophylactic manner at times or during periods (e.g., during a particular period of her cycle or at a particular time of the year) when she is especially prone to vaginitis or bacterial vaginosis. Additionally, these compositions may also be used in a prophylactic manner after menopause when normal vaginal secretions may decrease.

Preferably the polystyrene sulfonates used in the present invention are prepared by free radical polymerization of sodium styrene sulfonate, thereby essentially eliminating chlorinated hydrocarbon contamination. Even more preferably, the free radical polymerization of sodium styrene sulfonate is carried out in a system which is essentially free of cross-linking agents (e.g., divinylbenzene). Polystyrene sulfonate prepared by this method generally retains a high solubility in water, thereby making it easy to incorporate in aqueous-based formulations, including aqueous-based gel formulations. If desired, the polystyrene sulfonate salt can be spray dried to form a white fluffy powder which can easily be incorporated into such formulations. Preferably the polystyrene sulfonates used in the present invention have molecular weights greater than about 100,000 g/mole, and more preferably in the range of about 200,000 to about 1,000,000 g/mole. The expected structure of a preferred polystyrene sulfonates suitable is a follows:

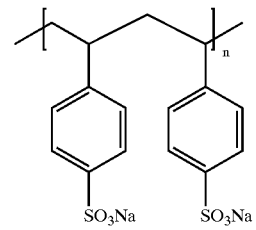

Although the sodium salts are generally preferred, other alkali metal salts, alkaline earth salts, or amine salts can be used.

The polystyrene sulfonates suitable for use in this invention can also be obtained commercially; such commercial preparations are, however, preferably further purified before use. For example, a polystyrene sulfonate having a molecular weight of about 500,000 to 700,000 g/mole is available from National Starch (Bridgeport, N.J.) under the tradename Versa-TL 502. Generally, polystyrene sulfonate intended for industrial use (e.g., as an antistatic or emulsifying agent) may contain low levels of dichloroethane (ranging from about 50 to 700 ppm). For use in the present method, it is preferable that the dichloroethane levels are reduced to less than about 50 ppm and more preferably to less than about 10 ppm using suitable purification techniques.

EXAMPLE 1

This example illustrates the preparation of sodium poly (4-styrene sulfonate) using a free-radical polymerization method. A 5 L reaction flask equipped with a mechanical stirrer and a reflux condenser was charged with 2 L of reagent grade water (Fisher ACS Reagent), 600 g of sodium 4-styrene sulfonic acid (Aldrich ACS Reagent), and 2.0 g of EDTA (Na$_2$.2H$_2$O) (Fisher ACS Reagent). The reaction was purged one hour with argon while being heated to about 60° C. An initiator solution was prepared by dissolving 17.2 g potassium persulfate (Fisher ACS Reagent) in 380 mL of reagent grade water (Fisher ACS Reagent). An aliquot of initiator solution (68 mL) was added to the reaction media over approximately 1 minute using an addition funnel. Aliquots of the initiator solution (68 mL) were added each hour for the next 3 hours (additions to this point 4×68 mL) while maintaining the reaction temperature at about 60° C. One hour after the fourth aliquot was added, the remaining initiator solution (about 100 mL) was added to the reaction mixture. Residual monomer levels were checked using HPLC. Approximately one hour after the final addition of initiator solution, the residual monomer level was less than about 2 percent. The reaction mixture was diluted with 1 L reagent water while cooling to room temperature. The resulting polymer solution was diluted and ultrafiltered until essentially all the residual monomer is removed. The resulting solution was spray dried affording approximately 333 g (about 56 percent yield) of white to off-white powder. Size exclusion chromatography of the solid affords a peak molecular weight (Mp) of about 800,000.

EXAMPLE 2

This example illustrates the inhibition of *Trichomonas vaginalis* using polystyrene sulfonate (sodium salt). The polystyrene sulfonate was prepared by the free radical polymerization of sodium styrene sulfonate as described in Example 1. The *Trichomonas vaginalis* organisms were grown in modified Diamond's medium using conventional techniques to produce an inoculum containing about $2 \times 10^3$ organisms per milliliter. Polystyrene sulfonate at 5.12 mg/ml was mixed was mixed with modified Diamond's medium to form a separate test solution. Various amounts of the inoculum were mixed with 2.1 ml aliquots of the polystyrene sulfonate test solution; the resulting samples were incubated anaerobically at 35° C. for about 16 to about 48 hours. The number of live *Trichomonas vaginalis* organisms were counted using a hemocytomer. Control samples (i.e., no added polystyrene sulfonate) were also evaluated in the same manner. The following results were obtained using 5.12 mg/ml polystyrene sulfonate:

| Incubation Time (hours) for PSS Samples | Number of Live Organisms | | | |
|---|---|---|---|---|
| | 400 μl Inoculum | 200 μl Inoculum | 100 μl Inoculum | 50 μl Inoculum |
| 16 | 55 | 10 | 0 | 0 |
| 24 | 60 | 50 | 4 | 3 |
| 40 | 70 | 50 | 4 | 0 |
| 48 | 35 | 75 | 2 | 5 |

The corresponding results for the control samples were as follows:

| Incubation Time (hours) for Control | Number of Live Organisms | | | |
|---|---|---|---|---|
| | 400 μl Inoculum | 200 μl Inoculum | 100 μl Inoculum | 50 μl Inoculum |
| 16 | 260 | 130 | 55 | 25 |
| 24 | 620 | 210 | 100 | 60 |
| 40 | tntc* | 850 | 360 | 130 |
| 48 | tntc* | tntc* | 500 | 250 |

*"to numerous to count"

EXAMPLE 3

This example illustrates the inhibition of *Gardnerella vaginalis* using the same polystyrene sulfonate (sodium salt) as in Example 2. *Gardnerella vaginalis* (ATCC 14018) was stored at −70° C. in skim milk (Difco Laboratories, Detroit, Mich.) and then cultured three times on V-Agar plates (Becton Dickinson Microbiology Systems, Cockeysville, Md.) prior to the inhibition studies. After overnight growth (about 16 hours) on a V-Agar plate, a fresh subculture sample of *G. vaginitis* was taken from several colonies using a sterile cotton swab. The subculture was suspended in sterile phosphate buffered saline (pH 72.2) to achieve a turbidity of 0.5 McFarland standard as determined by nephelometry; this corresponds to about $10^8$ CFU/ml. An inoculum suspension of about $10^7$ CFU/ml was obtained by dilution (about 1:10) using sterile phosphate buffered saline. Two HBT Bilayer Agar plates (Becton Dickinson Microbiology Systems) were inoculated by swabbing the entire surface with a cotton swab containing the inoculum. After inoculation, the plates were allowed to dry at ambient temperatures for about 2–3 minutes. Using a sterile, 10 mm diameter tube, three 10 mm wells were created in the agar on each plate. Samples (200 μl) were placed in each well. Two of the wells contained polystyrene sulfonate (10 mg/ml as described in Example 1) in water; the third well contained only sterile phosphate buffered saline. The plates were incubated at 37° C. under a five percent $CO_2$ atmosphere for 24 hours. The zone of inhibition around each well was measured to the nearest millimeter (from the edge of the well to the outer edge of the inhibition zone) at 12 and 24 hours. The following results were obtained:

| Sample | Growth-Inhibition Zone (mm) | |
|---|---|---|
| | 12 hours | 24 hours |
| Polystyrene Sulfonate | 6 | 6 |
| Control | 0 | 0 |

No hemolysis was observed with the polystyrene sulfonate samples.

Similar studies were carried out using other strains of *Gardnerella vaginitis* using similar procedures except that the zone of inhibition was only determined at 24 hours. The following results were obtained;

| | Zone of Inhibition (mm) at Polystyrene Sulfonate Concentration (mg/ml) | | | | | | | |
|---|---|---|---|---|---|---|---|---|
| Strain | 0* | 0.125* | 0.25* | 0.5* | 1.0* | 2.5* | 5.0* | 10* |
| 284 | 0 | 0 | 0 | 1.5 | 1.5 | 2.5 | 3.5 | 4 |
| 422 | 0 | 0 | 0.5 | 2 | 1.5 | 3 | 4.5 | 5 |
| 712 | 0 | 0 | 0 | 0.5 | 0.5 | 3.5 | 5 | 6 |
| 743 | 0 | 0 | 0 | 1 | 2 | 3 | 5 | 5.5 |

*Concentration of polystyrene sulfonate (mg/ml) in each well; 0 indicates control (sterile, phosphate buffered saline with no added polystyrenesulfonate).

EXAMPLE 4

This example illustrates the inhibition of other organisms using using the same polystyrene sulfonate (sodium salt) as in Example 2. In a first set of experiments, various concentrations of polystyrene sulfonate (sodium salt) in water were mixed with molten brucella agar supplemented with sheep blood, vitamin K, and hemin and then poured on separate plates. After the plates were dried, suspensions of the test organisms were spotted on the surface using a replicating device to obtain a final concentration of about 100,00 CFU/spot. After incubation at 37° C. for 48 hours under anaerobic conditions, the plates were examined for growth. For each organism tested, the lowest concentration of polystyrene sulfonate that inhibited growth was determined. The following results were obtained:

| Organism | Lowest PSS Concentration Inhibiting Growth |
|---|---|
| *Fusobacterium gonidiaformans* | 2.5 mg/ml |
| *Fusobacterium nucleatum* | 313 μg/ml |
| *Prevotella melaninogen* | 625 μg/ml |
| *Prevotella intermedia* | 625 μg/ml |
| *Prevotella bivia* | 1.25 mg/ml |
| *Prevotella. disiens* | 313 μg/ml |
| *Porphyromonas asaccharolytica* | 313 μg/ml |

| Organism | Lowest PSS Concentration Inhibiting Growth |
|---|---|
| Porphyromonas levii | 313 µg/ml |
| Pseudomonas asaccharolytica | 10 mg/ml |

In another set of experiments, polystyrene sulfonate (sodium salt) in various concentrations was prepared in brucella broth supplemented with sheep blood, vitamin K, and hemin. Aliquots (1 ml) of the polystyrene mixtures were then added to small plastic tubes. Test strains were prepared as ½ McFarland in brucella broth and diluted about 1:50 in brucella broth to obtain a concentration of about $3 \times 10^6$ CFU/ml. Samples (1 ml) of the test strains were added to the polystyrene sulfonate mixtures and then incubated for 2 days at 37° C. under anaerobic conditions. For each organism tested, the lowest concentration of polystyrene sulfonate that inhibited growth was determined. The following results were obtained:

| Organism | Lowest PSS Concentration Inhibiting Growth |
|---|---|
| Prevotella bivia | 1.25 mg/ml |
| Porphyromonas levii | 600 µg/ml |
| Bacteroides thetaiototaomicron | 5 mg/ml |

EXAMPLE 5

This example illustrates the inhibition of *Candida albicans* and other Candida species using the same polystyrene sulfonate (sodium salt) as in Example 2. A bioscreen broth microdilution test (National Committee for Clinical Standards inhibition assay NCCLS M27-T, 1995) was used; this assay relies on a computer-controlled incubator-reader (Bioscreen, Finland) and permits automated and continuous turbidometry of fungal growth. The polystyrene sulfonate was prepared in RPMI 1640 broth buffered with 0.165 mol/l MOPS. A working suspension of yeast inoculum ($1 \times 10^3$ to $5 \times 10^3$ CFU/ml) was made by 1:50 dilution of the ½ McFarland standard yeast suspension in saline followed by a 1:20 dilution with RPMI 1640 broth medium. The yeast suspension (150 ml) was diluted 1:1 with each polystyrene sulfonate solution (150 ml), achieving a final inoculum of $0.5 \times 10^3$ to $2.5 \times 10^3$ CFU/ml, before the wells were inoculated with the mixture. Fungal growth was determined after 16 hours at 37° C. by measuring the optical density; the optical density increases as fungal growth increases. The following results were obtained:

| Yeast | Optical Density as Function of Polystyrene Sulfonate (PSS) Concentration | | |
|---|---|---|---|
| | No PSS | 5 mg/ml PSS | 10 mg/ml PSS |
| Candida albicans* | 0.611 | 0.144 | 0.144 |
| Candida albicans* | 0.759 | 0.736 | 0.533 |
| Candida albicans* | 0.646 | 0.576 | 0.573 |
| Candida glabrata | 0.515 | 0.443 | 0.404 |
| Candida krusey | 0.604 | 0.581 | 0.516 |

*Yeast samples derived from different women.

These results suggest that *Candida albicans* from at least some women is effectively inhibited by polystyrene sulfonate. Other Candida species are also inhibited but somewhat less effectively.

EXAMPLE 6

This example reports on a clinical study sponsored by the Contraceptive Research and Development (CONRAD) program (Washington, D.C.) and performed at The CONRAD Clinical Research Center, Eastern Virginia Medical School (Norfolk, Va.) and Magee-Womens Hospital (Pittsburgh, Pa.). Four treatment regimes were used: 5% polystyrene sulfonate gel, 10% polystyrene sulfonate gel, vehicle alone (i.e., no active agent), and Conceptrol gel (a marketed product containing 4% nonoxynol-9), all at 2.5 ml per application. Forty-nine women were randomized to one of four treatment regimes (13 in the 5% polystyrene sulfonate gel group and 12 in each of the other groups) and were asked to use the assigned product for six consecutive nights at bedtime. Participants were not permitted to engage in intercourse during this period. The participants and investigators were blinded as to assignment. The women were examined at baseline and after the first and sixth applications.

No major changes occurred in laboratory parameters between screening and the last product use. This is consistent with the notion that polystyrene sulfonate is not absorbed from the vagina. No adverse experiences (i.e., serious or unexpected reactions related to product use) were observed in any of the groups. Only one woman (in the Conceptrol group) discontinued product use after the first administration, reporting irritation, burning, and itching of moderate to severe intensity. During the study, two to five women in each group reported itching, pain, and/or abnormal bleeding, with the fewest complaints in the 10% polystyrene sulfonate group and the most complaints in the Conceptrol group. Women in the Conceptrol group appeared to have the lowest subjective ratings of leakage and the lowest leakage based on the increase in weight of sanitary pads employed during product use.

Few abnormalities were noted on pelvic examination after six days of product use in any group. Although there were insufficient findings on pelvic examination to distinguish between the treatment groups, genital symptoms and urogenital adverse experiences were least common in the 10% polystyrene sulfonate group and most common in the Conceptrol group.

Using colposcopic examination, women in the Conceptrol group had the greatest number of product-related abnormal findings (i.e., eight women with a total of sixteen findings). Commonly associated terms for these findings are erythema, petechia/ecchymosis, and peeling. Of the remaining three groups, abnormal findings occurred most frequently in the vehicle group (five women with eight findings) and the least in the 10% polystyrene sulfonate group (one woman with a single finding). All product-related findings in the two polystyrene sulfonate groups were either intact epithelium/ not-intact blood vessel (petechiae/ecchymosis) type or not-intact epithelium/intact blood vessel (peeling) type. Overall, Conceptrol appeared to be the most irritating of the four study products, both after one use and after six uses. No significant differences between the other three products were noted after a single use. However, after six uses, the vehicle appeared to be significantly more irritating than the 5% and 10% polystyrene sulfonate gels.

Based on these studies, the overall the safety profile of polystyrene sulfonate appears to be very good.

EXAMPLE 7

This example illustrates preferred formulations for the inhibition or treatment of vaginitis and/or bacterial vaginosis in a female. Two especially preferred formulations are as follows:

|  | Formulation #1 | Formulation #2 |
| --- | --- | --- |
| Sodium Polystyrene Sulfonate | 5.0% | 10.0% |
| Glycerin | 11.0% | 11.0% |
| Propylene Glycol | 6.0% | 6.0% |
| Benzoic Acid | 0.2% | 0.2% |
| Methylparaben | 0.2% | 0.2% |
| Hydroxyethy Cellulose | 1.75% | 1.75% |
| Sodium Hydroxide | 0.04% | 0.04% |
| Water q.s. | balance | balance |

The formulations are prepared by simply blending the various ingredients. Generally, the sodium polystyrene sulfonate is in the range of about 1 to about 25 percent and the hydroxylethyl cellulose is in the range of about 0.5 to about 5 percent. The amount of sodium hydroxide is adjusted to provide a pH of about 3.5 to about 7.5. The hydroxylethyl cellulose functions as a gelling agent; other suitable gelling agents include, for example, sodium carboxymethyl cellulose, hydroxypropyl cellulose, hydroxylpropylmethyl cellulose, and the like. The amount of the other ingredients can be varied as desired.

All books, publications, patents, and patent applications referred to in the present specification are hereby incorporated by reference. The embodiments and examples described and discussed above are intended to illustrate the present invention and not to limit the scope of the invention which is defined in the appended claims.

That which is claimed is:

1. A method for the prevention, inhibition, or treatment of vaginitis and/or bacterial vaginosis in a female, said method comprising administering an effective amount of a polystyrene sulfonate composition into the vagina of the female, wherein the effective amount of polystyrene sulfonate is sufficient to inhibit Trichomonas, Gardnerella, Fusobacterium, Prevotella, Porphyromonas, Pseudomonas, or Bacteroides, and wherein the polystyrene sulfonate is soluble in water.

2. The method according to claim 1, wherein the polystyrene sulfonate composition comprises polystyrene sulfonate in an aqueous base buffered at a pH of about 3.5 to about 7.5.

3. The method according to claim 1, wherein the polystyrene sulfonate composition contains about 10 to about 250 mg/ml polystyrene sulfonate having a molecular weight greater than about 100,000 g/mole.

4. The method according to claim 2, wherein the polystyrene sulfonate composition contains about 10 to about 250 mg/ml polystyrene sulfonate having a molecular weight greater than about 100,000 g/mole.

5. The method according to claim 3, wherein the polystyrene sulfonate composition contains about 20 to about 100 mg/ml polystyrene sulfonate having a molecular weight greater than about 200,000 g/mole.

6. The method according to claim 4, wherein the polystyrene sulfonate composition contains about 20 to about 100 mg/ml polystyrene sulfonate having a molecular weight greater than about 200,000 g/mole.

7. A method for the control and inhibition of Trichomonas, Gardnerella, or other vaginitis/vaginosis-causing bacteria in the vagina of a female, said method comprising administering an effective amount of a polystyrene sulfonate composition into the vagina of the female, wherein the effective amount of polystyrene sulfonate is sufficient to control and inhibit Trichomonas, Gardnerella, Fusobactenum, Prevotella, Porphyromonas, Pseudomonas, or Bacteroides, and wherein the polystyrene sulfonate is soluble in water.

8. The method according to claim 7, wherein the polystyrene sulfonate composition comprises polystyrene sulfonate in an aqueous base buffered at a pH of about 3.5 to about 7.5.

9. The method according to claim 7, wherein the polystyrene sulfonate composition contains about 10 to about 250 mg/ml polystyrene sulfonate having a molecular weight greater than about 100,000 g/mole.

10. The method according to claim 8, wherein the polystyrene sulfonate composition contains about 10 to about 250 mg/ml polystyrene sulfonate having a molecular weight greater than about 100,000 g/mole.

11. The method according to claim 9, wherein the polystyrene sulfonate composition contains about 20 to about 100 mg/ml polystyrene sulfonate having a molecular weight greater than about 200,000 g/mole.

12. The method according to claim 10, wherein the polystyrene sulfonate composition contains about 20 to about 100 mg/ml polystyrene sulfonate having a molecular weight greater than about 200,000 g/mole.

13. A prophylactic treatment method for reducing the risk of vaginitis and/or bacterial vaginosis in a female, said method comprising administering an effective amount of a polystyrene sulfonate composition into the vagina of the female who may be at risk of vaginitis and/or bacterial vaginosis but is not suffering from vaginitis and/or bacterial vaginosis, wherein the effective amount of polystyrene sulfonate is sufficient to reduce the risk of Trichomonas, Gardnerella, Fusobacterium, Prevotella, Porphyromonas, Pseudomonas, or Bacteroides from becoming established within the vagina, and wherein the polystyrene sulfonate is soluble in water.

14. The prophylactic treatment method according to claim 13, wherein the polystyrene sulfonate composition comprises polystyrene sulfonate in an aqueous base buffered at a pH of about 3.5 to about 7.5.

15. The prophylactic treatment method according to claim 13, wherein the polystyrene sulfonate composition contains about 10 to about 250 mg/ml polystyrene sulfonate having a molecular weight greater than about 100,000 g/mole.

16. The prophylactic treatment method according to claim 14, wherein the polystyrene sulfonate composition contains about 10 to about 250 mg/ml polystyrene sulfonate having a molecular weight greater than about 100,000 g/mole.

17. The prophylactic treatment method according to claim 15, wherein the polystyrene sulfonate composition contains about 20 to about 100 mg/ml polystyrene sulfonate having a molecular weight greater than about 200,000 g/mole.

18. The prophylactic treatment method according to claim 16, wherein the polystyrene sulfonate composition contains about 20 to about 100 mg/ml polystyrene sulfonate having a molecular weight greater than about 200,000 g/mole.

19. A method for the selective prevention, inhibition, or treatment of vaginitis and/or bacterial vaginosis in a female without significantly disrupting normal vaginal flora, said method comprising administering an effective amount of a polystyrene sulfonate composition into the vagina of the female, wherein the effective amount of polystyrene sulfonate is sufficient to inhibit Trichomonas, Gardnerella, Fusobacterium, Prevotella, Porphyromonas, Pseudomonas, or Bacteroides without significantly disrupting normal vaginal flora, and wherein the polystyrene sulfonate is soluble in water.

20. The method according to claim 19, wherein the polystyrene sulfonate composition comprises polystyrene sulfonate in an aqueous base buffered at a pH of about 3.5 to about 7.5.

21. The method according to claim 19, wherein the polystyrene sulfonate composition contains about 10 to about 250 mg/ml polystyrene sulfonate having a molecular weight greater than about 100,000 g/mole.

22. The method according to claim 20, wherein the polystyrene sulfonate composition contains about 10 to about 250 mg/ml polystyrene sulfonate having a molecular weight greater than about 100,000 g/mole.

23. The method according to claim 21, wherein the polystyrene sulfonate composition contains about 20 to about 100 mg/ml polystyrene sulfonate having a molecular weight greater than about 200,000 g/mole.

24. The method according to claim 22, wherein the polystyrene sulfonate composition contains about 20 to about 100 mg/ml polystyrene sulfonate having a molecular weight greater than about 200,000 g/mole.

* * * * *